United States Patent

Manhes

[19]

[11] Patent Number: 6,162,239
[45] Date of Patent: Dec. 19, 2000

[54] INSTRUMENT WITH INDEPENDENT PLIERS

[75] Inventor: Hubert Manhes, Vichy, France

[73] Assignee: Karl Storz GmbH & Co. KG, Germany

[21] Appl. No.: 09/214,696

[22] PCT Filed: Jul. 11, 1997

[86] PCT No.: PCT/DE97/01468

§ 371 Date: Jun. 24, 1999

§ 102(e) Date: Jun. 24, 1999

[87] PCT Pub. No.: WO98/02103

PCT Pub. Date: Jan. 22, 1998

[30] Foreign Application Priority Data

Jul. 11, 1996 [DE] Germany .............. 196 27 992

[51] Int. Cl.$^7$ ................................................. A61B 17/00
[52] U.S. Cl. ............................................................ 606/205
[58] Field of Search ................... 606/1, 174, 205–210, 606/198, 142, 153

[56] References Cited

U.S. PATENT DOCUMENTS

| | | | |
|---|---|---|---|
| 5,099,827 | 3/1992 | Melzer et al. ........................ | 606/142 |
| 5,100,421 | 3/1992 | Christoudias . | |
| 5,236,437 | 8/1993 | Wilk et al. . | |
| 5,275,609 | 1/1994 | Pingleton et al. . | |
| 5,318,013 | 6/1994 | Wilk ................................... | 606/198 |
| 5,330,502 | 7/1994 | Hassire et al. ...................... | 606/174 |
| 5,423,813 | 6/1995 | Kaiser et al. . | |
| 5,423,830 | 6/1995 | Schnerbaum et al. . | |
| 5,527,332 | 6/1996 | Clement . | |
| 6,017,358 | 1/2000 | Yoon et al. ........................ | 606/174 |

FOREIGN PATENT DOCUMENTS

| | | |
|---|---|---|
| 4332238 | 12/1994 | Germany . |
| 4429478 | 3/1996 | Germany . |
| 1951258 | 7/1996 | Germany . |

OTHER PUBLICATIONS

J. J. Tibes and W. G. Leslie, "Arterial Replacement with Minimal Interruption of Blood Flow", The Lancet, Feb. 8, 1958, pp. 292–294.

Elsbeth Heinzelmann, "Intelligence Winzlinge für Die Chirurgie", Tranfyer Nr. 24, Jun. 20, 1994, pp. 48–52.

Primary Examiner—Michael Buiz
Assistant Examiner—William Lewis
Attorney, Agent, or Firm—St. Onge Steward Johnston & Reens LLC

[57] ABSTRACT

An instrument for application in endoscopic surgery has a shaft provided with a plurality of ducts, two of which receive forceps elements and at least one of which receives a surgical instrument for cooperation with the forceps elements. Each of the forceps elements has a distal end pivotal about a pivot axis which extends orthogonally to a longitudinal axis of the shaft, so that the distal ends of the forceps elements can be displaceable at a distance greater than on outer dimension of the shaft upon its insertion into a corporeal cavity.

18 Claims, 2 Drawing Sheets

INSTRUMENT WITH INDEPENDENT PLIERS

DESCRIPTION

1. Field of the Invention

The invention relates to an instrument for application in endoscopic surgical operations.

2. Prior art

An instrument having a shaft which receives two forceps, extending beyond a distal end of the shaft and pivotal toward and away from one another about an axis extending orthogonally to a longitudinal axis of the shaft is known from the German Patent DE 43 24 254 C1.

In quite a number of cases in endoscopic surgery it is now necessary to "contract" two tissue fragments which are separated from each other, to maintain them in this contracted state, and to unite them then, e.g. by a suturing or by an adhesive operation.

Examples of such operations may be found in surgical operations of torn ligaments in a joint such as the knee joint, or the in-vitro fertilisation of the fallopian tubes. Another example is described in the article by D. J. TIBBS et al. "Arterial Replacement with Minimal Interruption of Blood Flow", published in The Lancet, 1958, pp. 292 to 294".

The performance of these operations with conventional instruments requires not only comparatively long time but also a great manual skill of the physician performing the operation because the surgeon must handle several instruments introduced into the human body and co-ordinate their movements.

The instrument known from the German Patent DE 43 24 254 C1, too, is only conditionally suitable for the performance of such operations because the two bendable forceps, which are introduced separately of each other into a shaft including several ducts, do not allow for a coordinated movement in the sense of a selective approach of the two forceps to each other. Moreover, the individual ducts are disposed on the apeces of an equilateral triangle so that the manipulation of the contracted tissue fragment is rendered more complicated by an instrument introduced through the third duct. Moreover, the jaw elements present an inexpedient orientation relative to the pivoting axis so that a "contraction" of sensitive tissue fragments is not possible.

BRIEF DESCRIPTION OF THE INVENTION

The present invention is based on the problem of providing an instrument for application in endoscopic surgery, which will facilitate the "contraction" of two tissue fragments which are separate from each other, the holding of the tissue fragments in the contracted state and the subsequent manipulation, e.g. the connection by a suturing or adhesive process.

In accordance with the invention both forceps elements are each pivotable as a unit about parallel pivoting axes such that their mutual spacing in the direction of the transverse axis of the instrument may be varied. With these pivoting axes being at least approximately orthogonal on the longitudinal axis of the instrument the adjusting range for the spacing between the forceps elements is substantially greater than the diameter of the instrument which is restricted by the maximum "opening in the body" available.

Each of the forceps elements has a pair of jaws spaced from one another and extending from elements the distal discharge opening of a continuous duct so that (inter alia) a surgical instrument may be introduced in the duct for co-operation with the jaws of the two forceps elements.

With this inventive configuration the following method can be performed for connecting tissue fragments separated from each other:

The inventive instrument is introduced into the cavity where the tissue fragments to be united are located. The free ends of the tissue fragments, e.g. the fallopian tubes, are seized with the jaw of one respective forceps element of the instrument. Then the forceps jaws of the forceps elements are "approached to each other" in a direction orthogonal on the longitudinal axis of the instrument. With the two forceps elements of the instrument holding the tissue fragments, the free ends of the tissue fragments to be united are moved towards each other, too. As soon as the free ends have reached a position in which the bonding operation can be performed the operating physician performs the uniting operation. During the uniting operation and possibly even thereafter the parts to be united are held with the inventive instrument. The inventive instrument may, of course, be used also in other treatment or processing operations in the human or animal body or in engineering applications.

In accordance with another aspect of the invention the pivotable part(s) of the jaw of each forceps element is (are) pivotable about an axis which is orthogonal on the pivoting axis of the forceps element. This orientation, which is opposite to the orientation between the forceps jaws and the pivoting axis as it is known from the German Patent DE 43 24 254 C1, allows for the contraction of sensitive tissue fragments, too, because the jaw elements move approximately orthogonally on the direction in which the tissue fragments are moved when the forceps elements are pivoted.

In accordance with still anohter aspect of the invention a pivoting actuator element is mounted on the proximal end of the instrument for each forceps element, which, when operated, varies the pivoting angle and hence the distance between the forceps elements in the direction of the transverse axis. The variation of the pivoting angle does not take any influence on the mutual relative position of the jaw elements of each forceps element. It is thus possible to connect the free tissue fragments to be united towards each other with high precision and without any damage to the tissue.

According to yet another aspect of the invention the forceps elements are designed in the form of known forceps which are introduced, in particular, as a unit into a shaft. This configuration facilitates both the manufacture, stockkeeping at the manufacturing plant, and the cleaning of the inventive instrument. It is moreover expedient that the shaft presents the configuration of a known trocar or a laparoscope. This trocar shaft may have an outside diameter of 10 mm to 13 mm, e.g. when fallopian tubes are to be united.

It is moreover preferred, that the actuator elements for the jaw elements of the forceps are handle pieces—such as scissors handles, forceps handles or the like—which are biased into the position in which the respective forceps jaw is closed. This configuration presents the advantage that the physician need not hold the handle pieces in order to hold jaw elements of the two forceps in a closed condition when the tissue fragments are contracted.

The variation of the distance between the two forceps elements may be achieved in the most different ways on principle. It is possible, for instance, to hold at least one forceps element in a resilient and outwardly bent holder. Then the forceps element is "pushed inside" or the point of articulation is displaced by means of a linear guide or a sleeve.

In correspondence with the invention the forceps jaws are an element on flexible forceps known per se which have a distal end which is bendable in a way equally known per se.

The pivoting or bending movement of the forceps jaws may be achieved in the most different ways:

For instance, transfer elements such as sheathed cables, connecting rods or traction bars may be provided which transmit the movement of the actuator elements to the forceps jaws. It is moreover possible that distally disposed actuators are provided which create the pivoting or bending movement. The actuators may be micro control elements, particularly electrically operated elements, such as micro motors.

It is furthermore possible to use rigid forceps as forceps which have a distal end that can be bent as a unit and which comprise jaw elements which are connected via a rod or the like to a proximally disposed actuator element. In particular forceps may be used such as those described in the prior German Patent Application 196 25 241.5 of Karl Storz GmbH Co., Germany.

It is preferred that an equaliser mechanism is provided which prevents any variation of the relative angular position of the two jaw elements of the jaw when the distal end is bent or pivoted as a unit, respectively, because then the tissue can neither be damaged nor can slide out of the respective jaw element when the distance between the two forceps is varied.

When a rigid forceps element is used it is moreover preferred that the rod has a flexible configuration in the area of the bend in a manner known per se and closes the jaw in response to traction or pressure.

When a "rigid forceps" is used it is moreover preferable to provide a control element and specifically a set screw, by means of which element the distal end can be bent or pivoted, respectively, in response to operation of the element.

The set screw may be disposed at an angle of 90° relative to the longitudinal axis of the instrument or in a concentric position relative to the longitudinal axis of the instrument.

The manipulation of the inventive instrument is furthermore facilitated when certain angular positions of the two forceps are indexed or when the set screw presents catching means at certain angular positions.

The most different instruments may be inserted into the additional duct.

It is possible to use a suturing means upon introduction of a catheter.

When distal and proximal fallopian tube stumps are to be united, in particular, upon introduction of a catheter it is expedient that the adhesive means is a catheter which permits the application of a fibrin adhesive.

The forceps jaws of the inventive instrument may be designed, on principle, in any configuration known. It is particularly expedient, however, that each of the forceps jaws are formed by two clamping jaws. These clamping jaws may be provided with teeth so that the respective tissue fragments may be safely seized.

The shape of the clamping jaws may be matched with the tissue fragments to be united so as to achieve a large-area positive locking.

The adaptation to different surgery conditions is facilitated by the provision that the forceps jaws are additionally displaceable in the direction of the longitudinal axis of the instrument relative to the instrument body. The displacement of each forceps jaw may take place independently of the other forceps jaw. Due to the displaceability in the direction of the longitudinal axis it is possible, inter alia, to compensate for the angular offset which is caused as a result of the pivoting movement. If necessary, a forced guidance is also possible for a compensation of the angular offset.

BRIEF DESCRIPTION OF THE DRAWING

The invention will be described in the following, without any restriction of the general inventive idea, by exemplary embodiments, with reference to the drawing to which explicit reference is made in all other respects as far as the disclosure of all details is concerned which are not explained more thoroughly in the text. In the drawing.

DETAILED DESCRIPTION OF THE PREFERRED EMBODIMNET

Figure 1A:
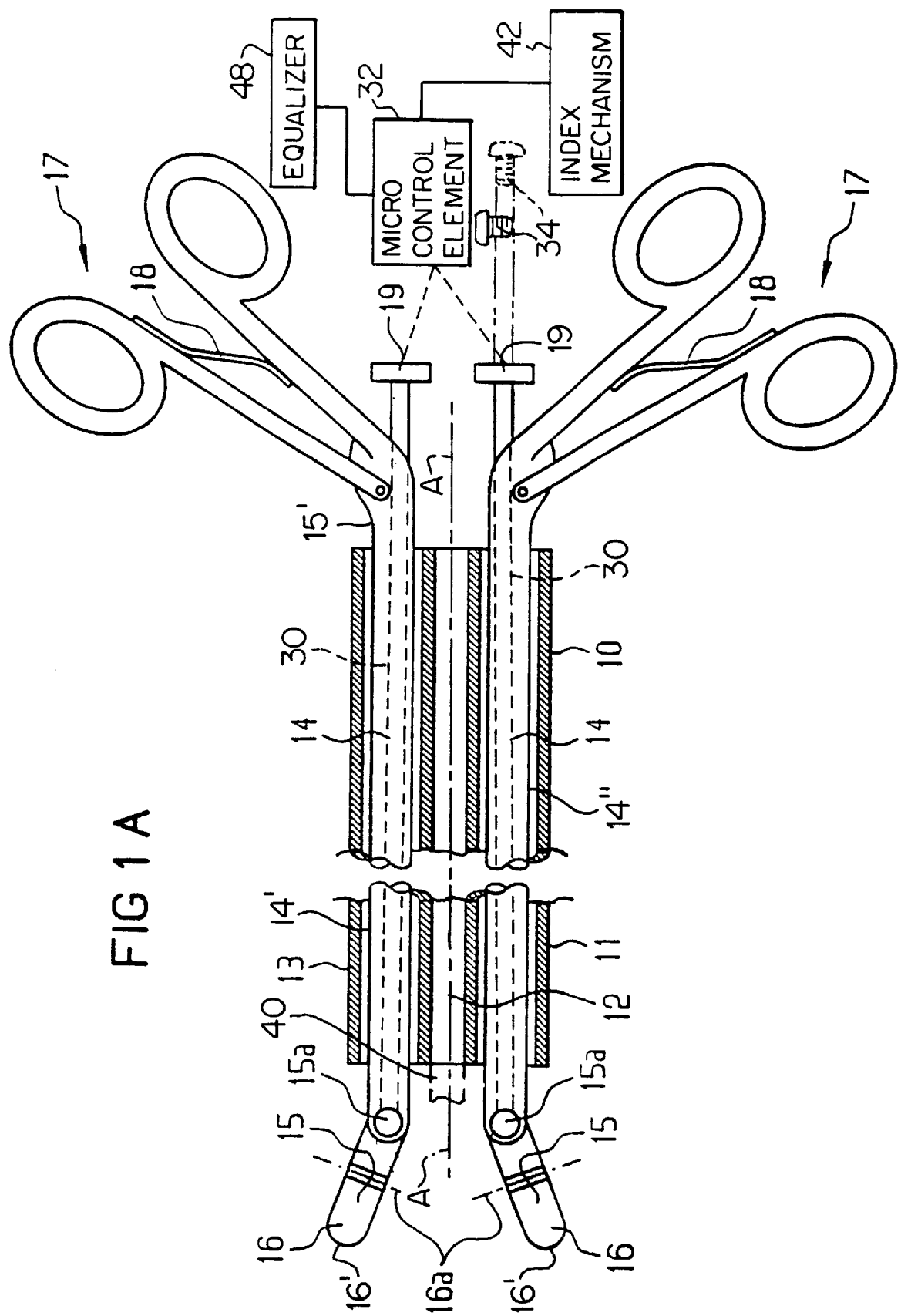
FIG. 1a side view of a first embodiment of an inventive instrument, partly as sectional view.

Referring to FIGS. 1A, B–2A,B a surgical instrument, in accordance with the invention, allows a surgeon to affix two tissue fragments 40, 42 (FIG. 2A) to one another. Particularly, the surgical instrument includes a trocar sleeve or shaft 13 having two spaced apart ducts 14 which define a space therebetween that receives a third duct 12 shaped to house an instrument 40 (FIG. 1A). As an example, a catheter delivering an adhesive, a suturing instrument or any other surgical instrument cooperating with a pair of forceps elements 14', 14" during the surgery can be used as the instrument inserted in the third duct 12.

Each of the forceps elements can be selected from a great variety of clamping tools, such as scissors and the like, and typically includes a body extending between proximal 15' and distal 16 ends. According to the invention, the distal end 16 is pivotally mounted to the forceps element so as a distance between distal tips 16' can vary.

In order to operate the forceps elements including the distal ends thereof, the instrument has a pair of actuators 19, each connected to the respective proximal end 15' and performing several functions. Firstly, each of the ducts 14 is shaped to allow the forceps element to be linearly displaced therein parallel to a longitudinal axis A—A of the instrument upon applying an external force to the actuator 19. Secondly, actuators are provided with transmitting elements 30 transferring motion of the actuator 19 to pivotal displacement of the distal end 16 about an axis 15a, which extends orthogonal to the longitudinal axis A—A. As a result, a distance at which the distal tips can be spaced from one another is greater than a diameter of the trocar sleeve 13 during a clamping phase.

The actuator 19 can be selected among micro-control elements 32, such as a micro motor, or a set screw 34 or any other element providing a controllable displacement of the distal ends in response to actuating of the actuator 19. A relative position of the set screw relative to the longitudinal axis A—A can vary between a coaxial position of the set screw and the ducts and a position wherein the set screw extends perpendicular to the longitudinal axis.

Figure 2A:
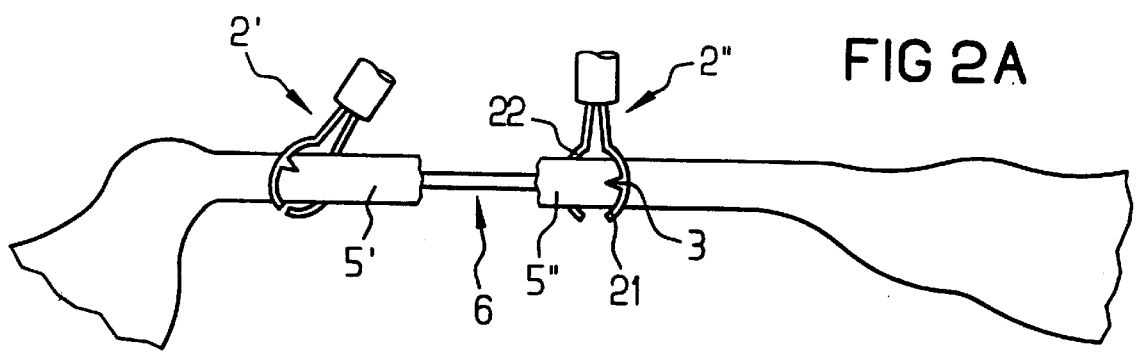
FIGS. 2a and 2b show each an illustration for explanation of the application of is instrument.
Figure 2B:
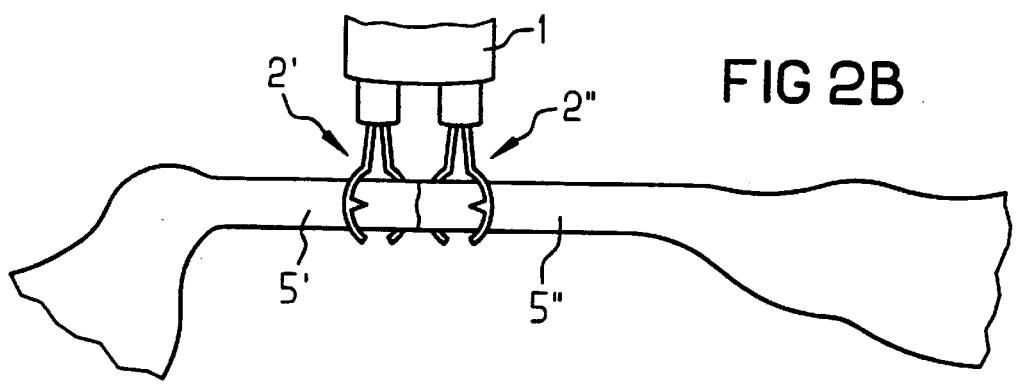

As mentioned above, the present invention is particularly suitable for facilitating contraction of two tissue fragments necessitating, thus, transferring of the actuator's motion to the pivotal displacement of the distal ends from a position shown in FIG. 1A to a position illustrated in FIG. 2B. Given purely as an example, the transmitting element 30 can be selected form the group including sheathed cables, connecting rods and traction bars.

Pivotal displacement of the distal ends 16 can be controllable by having an index mechanism 42 which is connected to the actuator, thereby allowing a surgeon to precisely operate the latter in order to displace the distal end at a desirable angle.

According to another aspect of the invention, each distal end 16 is adapted to grip a tissue fragment. Particularly, each distal end has a pair of jaws 15 (FIG. 1A) displaceable relative to one another about a bending axis 16a which is coplanar with but orthogonal to the longitudinal axis A—A. Further, the bending axis lies in a plane extending orthogonally to the pivot axes. Thus, as shown in FIG. 1A, the jaws are closed, but can be open by another actuator 17, which is mounted to the proximal end 15' of the forceps and connected to the distal end thereof by one of the above-mentioned transferring elements 30. Each of the jaws is preferably shaped to have a gripping surface shaped substantially complimentary to a segment of a tissue to be gripped. Thus, for example, if distal and proximal fallopian stumps are to be united, as shown in FIGS. 2A—2B, the gripping surfaces 21' (FIG. 1B) of the jaws 21, 22 are curved to extend substantially along the stump's periphery in the closed position of the jaws. Each of the gripping surfaces can be provided with a tooth 44 (FIG. 1B) to ensure engagement between the jaws and the fallopian stump to be displaced.

The actuator 17 is a scissors-like handle provided with a spring 18 which biases the scissors levers toward one another, as shown in FIIG. 1A. This position corresponds to the closed position of the jaws 15, thereby facilitating introduction of the forceps into a corporeal cavity as a result of a compact structure of the distal ends.

To compensate for the angular offset as a result of the pivoting motion of the distal ends 16, the instrument has an equalizer 48 connected to the actuator 19 to linearly displace the forceps elements 14 along the longitudinal axis A—A after or during its angular displacement. It should be noted that the axial displacement of the forceps, pivoting of the distal ends 16 and relative displacement of the jaws 15 of each pair can be monitored. Thus, each part of one the forceps element can be controlled individually or synchronously with the identical part of the other forceps element.

Figure 1B:
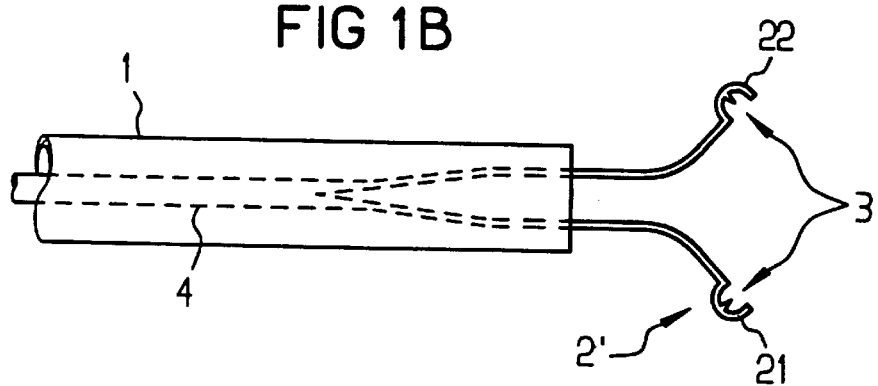
FIG. 1b is a schematic illustration of a second embodiment.

Referring specifically to FIG. 1B, instead of having rigid forceps elements and actuators 17 displacing the jaws 21, 22 relative one another, the forceps can be made flexible to have the jaws 21 and 22 approach each other (FIGS. 2A,B). Such displacement may be implemented by using, for example, outer sleeves 46 (FIGS. 1B and 2A) displaceable relative to the flexible forceps elements and having an inner diameter which is smaller than a distance at which the distal ends can be spread apart. The actuator 19 is connected to the proximal end of the forceps element via the transferring element 30 to displace the latter within the duct 14 which frictionally guides the jaws between open and closed positions, as seen in FIGS. 1B and 2A, respectively.

To implement the pivoting of distal ends, at least one of the forceps elements has a bend 54 (FIG. 2A) resiliently pivoting the distal end about a pivot axis 3 which extends perpendicular to the longitudinal axis A—A at a predetermined angle. Such structure allows the distal ends 2' and 2" to move between a position shown in 2A to a position illustrated by FIG. 2B, wherein the distal ends extend parallel to one another upon withdrawal of the forceps elements towards a proximal end of the shaft.

FIGS. 2A–2B illustrate a process of adhering two tissue segments 50, 52 gripped by the pair jaws upon pivotal displacement of the distal ends from one another at a maximum distance that, as shown in FIG. 2A can exceed an outer diameter of the shaft 10. As the actuator 19 linearly displaces the forceps elements toward the proximal end of the shaft 1 by means of transfer elements 4 (FIG. 1B), at least one distal end 2' is frictionally guided against the conduit 14 to pivot about the axis 3. Upon overcoming a lateral force exerted by the bend 54, the distal ends 2' and 2" of the forceps elements assume a position shown in FIG. 2B, wherein the distal ends are brought close to one another upon pivoting of at least one distal end 2'. Upon closing the tissue segments, the catheter 40 containing an adhesive is introduced in the duct 12 to adhere the meeting ends of the fragments together.

It is understood that shapes of the jaws can vary depending on a particular surgical procedure performed by the disclosed instrument. Accordingly, the drawings and description herein are preferred by way of example and do not limit the scope of the invention as defined in the following claims.

What is claimed is:

1. An endoscopic surgical instrument, comprising:
   a shaft having an exterior extending along a longitudinal axis which lies in a first plane;
   a plurality of separate axially extending ducts in said exterior;
   a pair of spaced apart forceps elements, each received in a respective one of the ducts and having distal and proximal ends, each distal end being pivotal relative to the proximal end about a respective pivot axis extending in a second plane perpendicular to the first one;
   a pair of jaws mounted on each of the distal ends of the forceps elements and displaceable relative to one another about a bending axis which lies in the first plane and extends transversely to the longitudinal axis;
   a pair of first actuators, each connected to the respective proximal end of the forceps elements to move the jaws of each pair toward and away from one another about said bending axis,
   a pair of second actuators, each connected to the proximal end of the respective forceps element and pivoting the distal end between a first position, wherein the distal ends are spaced at a first distance, and a second position, wherein the distal ends are spaced apart at a second distance which is less than the first one; and
   a surgical instrument received in the duct between the forceps elements for cooperation with the distal ends of the of the forceps elements.

2. The instrument defined in claim 1, wherein the shaft has an outer dimension, said first distance of the distal ends being greater than the outer dimension of the shaft.

3. The instrument defined in claim 1, wherein each the second actuators is selected from the group consisting of an electrical micro-control element and a set screw.

4. The instrument defined in claim 3, herein each of the fist actuators is a handle having a pair of actuating levers and a spring between the levers to bias them from a working position, wherein the jaws are open, to a rest position, wherein the jaws are closed.

5. The instrument defined in claim 3 wherein each of the second actuators linearly displaces the respective forceps element parallel to the longitudinal axis to have the distal ends extend beyond the duct.

6. The instrument defined in claim 5 wherein the jaws of each pair are biased away from one another upon extending from the respective duct.

7. The instrument defined in claim 3 wherein each of the first and second actuators includes a transmitting element transferring motion of the actuator to pivotal displacement of the distal end and to the displacement of jaws, respectively, the transmitting element being selected from the group consisting of sheathed cables, connecting rods and traction bars.

8. The instrument defined in claim 3 wherein each of the second actuators includes an indexing mechanism to controllably pivot the distal end to a predetermined angular position.

9. The instrument defined in claim 1 wherein the shaft is a trocar shaft having an outer diameter which varies from 10 to 13 mm.

10. The instrument defined in claim 1 wherein the surgical instrument selected from the group consisting of suturing and catheter element, the catheter element is shaped to deliver a fibrin adhesive.

11. The instrument defined in claim 1 wherein each jaw has at least one clamping tooth, each pair of jaws being shaped to conform to an organ to be gripped in the closed position of the jaws.

12. The instrument defined in claim 3, further comprising an equalizer connected to the one and other further actuators to compensate for the variations of axial distance between the proximal and distal ends of each forceps element during pivoting of the distal end.

13. An endoscopic surgical instrument, comprising:

a shaft having an exterior extending along a longitudinal axis;

a plurality of separate axially extending ducts in said exterior;

a pair of spaced apart forceps elements, each being received in a respective one of the ducts and having distal and proximal ends, each distal end having a flexible bend resiliently biasing the distal end away from the distal end of the other forceps element about a pivot axis which extends perpendicular to the first one, so that the distal ends are pivotal between a first position, wherein the distal ends are spaced at a first distance, and a second position, wherein the distal ends move toward one another from the first position;

a plurality of jaws grouped in pairs, each of which being mounted on the distal end of the respective forceps element;

a pair of jaw actuators, each mounted on the proximal end of the respective forceps element and actuating the jaws of the respective pair so as to enable the jaws to displace relative to one another about a bending axis which extends orthogonally to the pivot and longitudinal axes; and a surgical instrument received in the duct between the forceps elements for cooperation with the distal ends of the of the forceps elements.

14. The instrument defined in claim 13, further comprising a pair of bend actuators, each connected to the distal end of the respective forceps element for linearly displacing the forceps elements as the distal ends pivot between the first and second positions.

15. The instrument defined in claim 13 wherein the bend is made of resilient material biasing the distal end radially outwardly to the first position, the distal ends assuming the second position as the forceps elements are withdrawn in the ducts upon linear displacement thereof toward the proximal ends.

16. The instrument defied in claim 15 wherein each of the flexible forceps elements is frictionally guided against the respective duct to overcome a force exerted by the bend to assume the second position, wherein the forceps elements extend substantially parallel to the longitudinal axis.

17. An endoscopic surgical instrument, comprising:

a shaft having extending along a longitudinal axis;

a plurality of separate axially extending ducts in said shaft;

a pair of spaced apart forceps elements, each received in a respective one of the ducts and having distal and proximal ends, each distal end being pivotal relative to the proximal end about a respective pivot axis perpendicular to the first one, and having a respective pair of jaws displaceable relative to one another;

at least one first actuator connected to the proximal end of one of the forceps elements to pivot the distal end of the one forceps element between a first position, wherein the distal end of the one forceps element is spaced from the distal end of the other forceps element at a first distance, and a second position, wherein the distal ends are spaced apart at a second distance which is less than the first one;

a pair of second actuators, each actuating the respective pair of jaws between a rest position, wherein the jaws are closed, and an open position, each of the second actuators having a pair of handles biased from one another to move the jaws in the rest position; and a surgical instrument received in the duct between the forceps elements for cooperation with the distal ends of the of the forceps elements.

18. An endoscopic surgical instrument, comprising:

a shaft having an exterior extending along a longitudinal axis which lies in a first plane;

a plurality of separate axially extending ducts in said exterior;

a pair of spaced apart forceps elements, each being received in a respective one of the ducts and having distal and proximal ends, each distal end being pivotal relative to the proximal end about a respective pivot axis extending in a second plane perpendicular to the first one;

at least one first actuator pivoting the distal end of one of the forceps elements between a first position, wherein the distal end of the one forceps element is displaced from the distal end of the other forceps element at a first distance, and a second position, wherein the distal end of the one forceps element is displaced at a second distance from the distal end of the other forceps element, said second distance being less than the first one; and a surgical instrument received in the duct between the forceps elements for cooperation with the distal ends of the of the forceps elements.

* * * * *